United States Patent
Cho et al.

(10) Patent No.: US 12,201,423 B2
(45) Date of Patent: Jan. 21, 2025

(54) UNIT FOR COLLECTING AND EJECTING BLOOD

(71) Applicant: HLB LIFE SCIENCE CO., LTD., Hwaseong-si (KR)

(72) Inventors: Yong Ho Cho, Suwon-si (KR); Young Joo Moon, Suwon-si (KR); Woong Ho Lee, Yongin-si (KR)

(73) Assignee: HLB LIFE SCIENCE CO., LTD., Hwaseong-si (KR)

( * ) Notice: Subject to any disclaimer, the term of this patent is extended or adjusted under 35 U.S.C. 154(b) by 1026 days.

(21) Appl. No.: 17/030,535

(22) Filed: Sep. 24, 2020

(65) Prior Publication Data

US 2021/0100487 A1    Apr. 8, 2021

(30) Foreign Application Priority Data

Oct. 4, 2019   (KR) .......................... 10-2019-0122929

(51) Int. Cl.
*A61B 5/15*    (2006.01)

(52) U.S. Cl.
CPC .. *A61B 5/150236* (2013.01); *A61B 5/150343* (2013.01); *A61B 5/150351* (2013.01); *A61B 5/150419* (2013.01)

(58) Field of Classification Search
CPC .......... A61B 5/15134; A61B 5/150419; A61B 5/15045; A61B 5/150343;

(Continued)

(56) References Cited

U.S. PATENT DOCUMENTS

| 4,003,262 A * | 1/1977 | Gerarde ................. B01L 3/021 |
| | | 422/922 |
| 4,023,716 A * | 5/1977 | Shapiro ................ B01L 3/0279 |
| | | 422/932 |

(Continued)

FOREIGN PATENT DOCUMENTS

| CN | 103 429 155 A | 12/2013 |
| CN | 108 780 028 A | 11/2018 |

(Continued)

OTHER PUBLICATIONS

Chinese Office Action Corresponding to 202011016490.6 mailed Oct. 26, 2023.

*Primary Examiner* — Rene T Towa
*Assistant Examiner* — H. Q. Nguyen
(74) *Attorney, Agent, or Firm* — Finch & Maloney PLLC

(57) ABSTRACT

Disclosed herein is a unit for collecting and ejecting blood including: a handle extending along a first central axis; a handling block connected to the handle and disposed to have a second central axis that is offset from the first central axis; and a plunger connected to the handle to be movable along a direction of the first central axis and moving toward the handling block when manipulated, wherein the handling block includes: a body having a connection portion connected to the handle and a contact portion located beneath the connection portion; and a collection port formed to pass through the body in a direction from the contact portion to the connection portion and configured to collect blood by a capillary force, and the plunger moves along the direction of the first central axis when manipulated to enter the collection port and push the blood collected in the collection port out of the collection port.

6 Claims, 3 Drawing Sheets

(58) Field of Classification Search
CPC ........ A61B 5/150236; A61B 5/150244; B01L 3/022–0224; B01L 3/021; B01L 9/54; B01L 9/543; B01L 9/06; B01L 9/065; A61M 5/31531
USPC ...................................................... 73/864.13
See application file for complete search history.

(56) References Cited

U.S. PATENT DOCUMENTS

| | | | |
|---|---|---|---|
| 5,059,398 A * | 10/1991 | Kenney | A61B 5/150213 422/922 |
| 8,852,123 B2 | 10/2014 | Roe et al. | |
| 2001/0016358 A1 * | 8/2001 | Osawa | B01L 3/0217 436/180 |
| 2009/0299224 A1 | 12/2009 | Yoo | |
| 2019/0159710 A1 | 5/2019 | Iwasawa et al. | |

FOREIGN PATENT DOCUMENTS

| | | | | |
|---|---|---|---|---|
| EP | 0 209 705 A2 | 1/1987 | | |
| KR | 10 2006 0128274 A | 5/2007 | | |
| WO | WO-9944744 A1 * | 9/1999 | .............. | B01L 3/021 |

* cited by examiner

UNIT FOR COLLECTING AND EJECTING BLOOD

CROSS REFERENCE TO RELATED APPLICATION

This application claims the benefit of Korean Patent Application No. 10-2019-0122929, filed on Oct. 4, 2019, entitled "Unit for Collecting and Ejecting Blood", which is hereby incorporated by reference in its entirety into this application.

BACKGROUND

Field

The present invention relates to a unit for collecting and ejecting blood in a non-invasive form for an instant blood test.

Description of the Related Art

With the development of medical technology, various kinds of diseases can be diagnosed by blood tests. As a way of collecting blood for a blood test, a syringe is typically used. However, the syringe may cause great pain to a subject from whom blood is collected because the blood is drawn in a state where a needle of the syringe penetrates into a human body.

Unlike blood collection using a syringe, a non-invasive collection device is also used to collect blood that is taken out after a small wound is made on a finger or the like with a lancet. The non-invasive collection device is used mainly to collect a small amount of blood, and does not cause great pain to a subject from whom blood is collected.

In spite of this advantage, in a conventional cup-shaped blood collector that has a large depth, which is used according to an increase in an amount of blood to be collected, an air layer may be formed inside the cup-shaped structure. Blood collection is disrupted by the air layer, and it is not possible to accurately collect a desired amount of blood.

Furthermore, the collected blood should be naturally released to an absorption pad of a test device, but when a size of a blood dropping portion in the test device is small, the blood does not reach the absorption pad, resulting in a problem in that the blood is not smoothly released.

SUMMARY

An object of the present invention is to provide a unit for collecting and ejecting blood using a capillary phenomenon, while not structurally causing a restriction by an air layer in collecting a desired amount of blood.

Another object of the present invention is to provide a unit for collecting and ejecting blood capable of effectively ejecting the collected blood in a different way than a natural release.

According to an exemplary embodiment of the present invention, there is provided a unit for collecting and ejecting blood including: a handle extending along a first central axis; a handling block connected to the handle and disposed to have a second central axis that is offset from the first central axis; and a plunger connected to the handle to be movable along a direction of the first central axis and moving toward the handling block when manipulated, wherein the handling block includes: a body having a connection portion connected to the handle and a contact portion located beneath the connection portion; and a collection port formed to pass through the body in a direction from the contact portion to the connection portion and configured to collect blood by a capillary force, and the plunger moves along the direction of the first central axis when manipulated to enter the collection port and push the blood collected in the collection port out of the collection port.

The handle may include: a main portion extending along the first central axis; and a rail formed on the main portion and extending along the direction of the first central axis, and the plunger may include a slider slidably coupled to the rail along the direction of the first central axis.

The handle may include stoppers formed on the main portion and stopping the plunger at preset positions, the stoppers including: a first stopper stopping the plunger at a first position that is a position before the plunger enters the collection port; and a second stopper stopping the plunger at a second position that is a position after the plunger enters the collection port.

The first stopper may be formed to protrude at a height allowing the plunger to pass therethrough, and the second stopper may be formed to protrude at a height not allowing the plunger to pass therethrough.

According to another exemplary embodiment of the present invention, there is provided a unit for collecting and ejecting blood including: a handle having a length to be gripped in a hand of a user; a handling block including a body connected to the handle and a collection port formed to pass through the body in a vertical direction to collect blood by a capillary force; and a plunger movably installed on the handle to be inserted into the collection port and ejecting the blood collected in the collection port out of the collection port.

The handle may include: a main portion extending along a length direction; and a rail formed on the main portion and extending along the lengthwise direction, and the plunger may include a slider slidably coupled to the rail along the length direction.

The rail may include a rib protruding from the main portion in a radial direction, and the slider may include a receiving groove receiving the rib and extending along the length direction.

The handle may include stoppers formed on the main portion and stopping the plunger at preset positions.

The stoppers may include: a first stopper stopping the plunger at a first position that is a position before the plunger enters the collection port; and a second stopper stopping the plunger at a second position that is a position after the plunger enters the collection port.

The plunger may further include a rod connected to the slider and disposed to be inserted into the collection port.

The plunger may further include a squeezing plate installed at a front end of the rod and elastically deformed while having a larger cross-sectional area than the rod.

DETAILED DESCRIPTION

Figure 1:
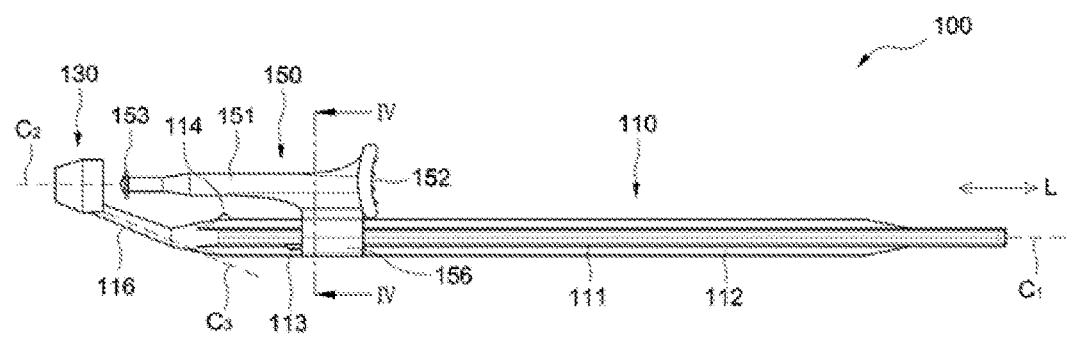
FIG. 1 is a front view of a unit 100 for collecting and ejecting blood according to an exemplary embodiment of the present invention.

Hereinafter, a unit for collecting and ejecting blood according to a preferred exemplary embodiment of the present invention will be described in detail with reference to the accompanying drawings. Throughout the present specification, the same or similar reference numerals denote the same or similar components even in different exemplary embodiments. Once the same or similar components are described, the description thereof will not be repeated.

FIG. 1 is a front view of a unit 100 for collecting and ejecting blood according to an exemplary embodiment of the present invention.

Referring to FIG. 1, the unit 100 for collecting and ejecting blood may include a handle 110, a handling block 130, and a plunger 150.

The handle 110 is a part used to be gripped in a hand of a user. To this end, the handle 110 may have a generally elongated rod shape. Specifically, the handle 110 may include a main portion 111 and a sub portion 116.

The main portion 111 may be longer than the sub portion 116. The main portion 111 may have a main axis or a first central axis $C_1$ as an extension reference. A rail 112 extending along a direction of the first central axis $C_1$ may be formed on the main portion 111. The rail 112 may be a rib protruding in a radial direction of the main portion 111. The rib may have a generally rectangular plate shape. In addition, the number of ribs may be plural. In the present exemplary embodiment, four ribs are formed at intervals of 90°.

Stoppers 113 and 114 may also be formed on the main portion 111. The stoppers 113 and 114 are configured to stop the plunger 150 at preset positions while the plunger 150 moves along the main portion 111 when manipulated. The stoppers 113 and 114 may be formed as protrusions protruding from the main portion 111, in particular the rail 112. The stoppers 113 and 114 may be divided specifically into a first stopper 113 and a second stopper 114. The first stopper 113 is for stopping the plunger 150 at a position (a first position) before the plunger 150 enters a collection port 135 (see FIG. 2), and the second stopper 114 is for stopping the plunger 150 at a position (a second position) after the plunger 150 enters the collection port 135. Here, the second position may be a position within the collection port 135 or a position at which an end (e.g. a squeezing plate 153) of the plunger 150 is placed outside the collection port 135 after passing through the collection port 135. Furthermore, the first stopper 113 may be formed to protrude at a height for the plunger 150, in particular a slider 156, to be caught thereby but pass therethrough by a user's force. In contrast, the second stopper 114 may protrude at a height not allowing the slider 156 to pass therethrough.

The sub portion 116 is a part connecting the main portion 111 and the handling block 130. When the sub portion 116 extends along a sub axis or a third central axis $C_3$, the third central axis Cs may have an arrangement relationship to be inclined with respect to the first central axis $C_1$.

The handling block 130 is configured to collect blood by being in contact with the blood or eject the collected blood to an absorption pad of a diagnostic device. The handling block 130 may be connected to an end of the handle 110, in particular the sub portion 116, so that the handling block 130 may be located at one end of the unit 100 for collecting and ejecting blood. The handling block 130 may also be disposed along a second central axis $C_2$. Here, the second central axis $C_2$ may be offset from the first central axis $C_1$.

The plunger 150 is installed on the handle 110, in particular the main portion 111, to be movable when manipulated. The plunger 150 is disposed to move toward the handling block 130 when manipulated. Specifically, the plunger 150 may have a rod 151 to be inserted into the collection port 135 of the handling block 130. The rod 151 may have a manipulation portion 152 to be pushed by a user at an end thereof. The rod 151 may have the squeezing plate 153 at the other end thereof. The squeezing plate 153 is elastically deformed by being forcedly fitted into the collection port 135, and thus, is in tight contact with an inner surface defining the collection port 135 of the handling block 130. To this end, the squeezing plate 153 may have a larger cross-sectional area than the rod 151. The slider 156 protrudes from the rod 151 toward the main portion 111. The slider 156 is slidably coupled to the rail 112 along the direction of the first central axis $C_1$.

The specific configuration of the above-described unit 100 for collecting and ejecting blood will be described with reference to FIGS. 2 to 4.

Figure 2:
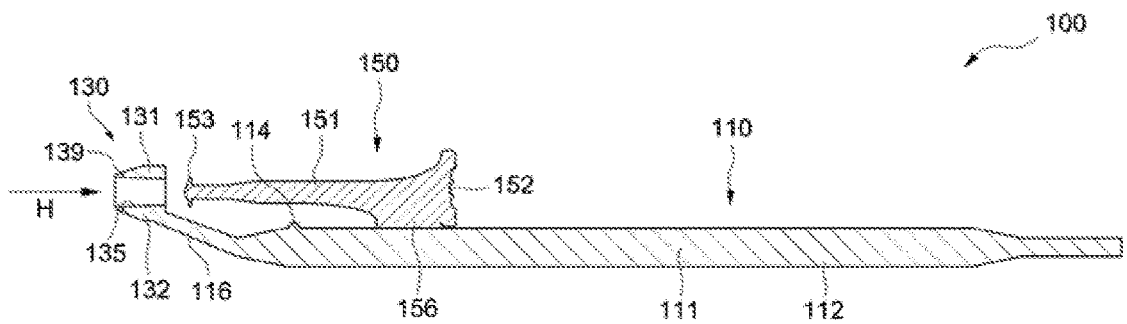
FIG. 2 is a cross-sectional view of the unit 100 for collecting and ejecting blood of FIG. 1.
Figure 3:
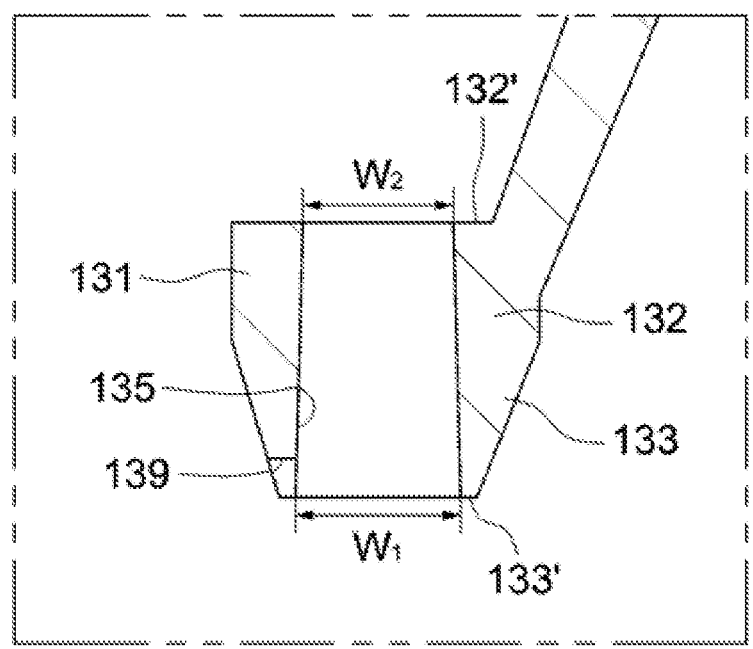
FIG. 3 is a partially enlarged cross-sectional view of a handling block 130 of FIG. 2.

FIG. 2 is a cross-sectional view of the unit 100 for collecting and ejecting blood of FIG. 1, and FIG. 3 is a partially enlarged cross-sectional view of the handling block 130 of FIG. 2.

Referring to FIGS. 2 and 3, the handling block 130 may include a body 131, the collection port 135, and an ejection groove 139.

The body 131 may have a generally cylindrical shape. Specifically, the body 131 may include a connection portion 132 and a contact portion 133. The connection portion 132 is located in an upper portion of the body 131 and connected to the sub portion 116. The contact portion 133, which is located in a lower portion of the body 131, is a part that is brought into contact with a finger of a subject to be diagnosed or the absorption pad of the diagnostic device.

The contact portion 133 may have a cross-sectional area that is gradually smaller as being farther away from the connection portion 132. Thus, a width of a lower end 133' of the contact portion 133 is smaller than that of an upper end 132' of the connection portion 132. Due to the tapered shape of the contact portion 133, when the contact portion 133 is in contact with a finger from which blood is drawn, it is possible to minimize an amount of blood that is contact with the bottom of the contact portion 133 other than the collection port 135. As a result, it is possible to accurately adjust an amount of blood collected from the subject to be diagnosed to an amount set by the collection port 135, thereby minimizing a deviation in the amount of blood collected each time.

The collection port 135 is an open hole formed to pass through the body 131 in a vertical direction. Specifically, the collection port 135 may be continuously formed from the lower end 133' of the contact portion 133 to the upper end 132' of the connection portion 132. The direction from the lower end 133' to the upper end 132' may be defined as a collection direction H.

The collection port 135 may have a cross-sectional area that is gradually smaller from the contact portion 133 to the connection portion 132 along the collection direction H. Thus, a width $W_1$ of the lower end 133' is larger than a width $W_2$ of the upper end 132'. According to this configuration, the width of the collection port 135 decreases to cope with the capillary force that is gradually smaller as it becomes closer to the upper end 132' along the collection direction H in the collection port 135 when blood is collected using the action of capillary force, thereby supplementing the capillary force such that the blood moves up to the upper end 132'.

An ejection groove 139 is configured to facilitate ejection of the blood collected in the collection port 135 into the absorption pad of the diagnostic device. The ejection groove 139 may be formed in the lower end 133' of the contact portion 133.

The configuration of the slider 156 of the plunger 150 will be described with reference to FIG. 4.

Figure 4:
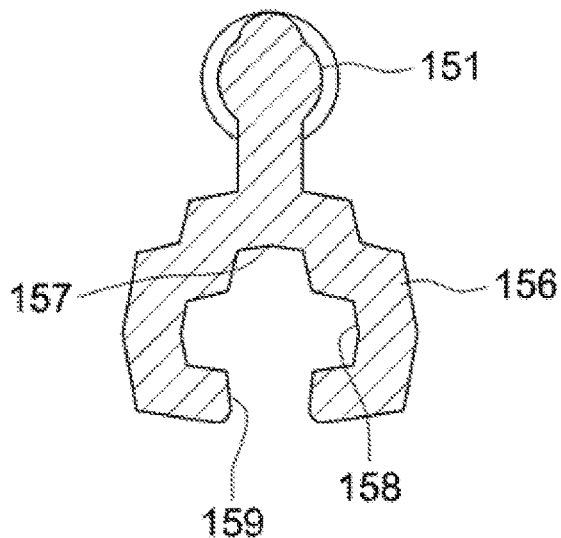
FIG. 4 is a cross-sectional view of a plunger 150 taken along line IV-IV of FIG. 1.

FIG. 4 is a cross-sectional view of the plunger 150 taken along line IV-IV of FIG. 1.

Referring to FIG. 4, the slider 156 of the plunger 150 may have receiving grooves 157 and 158 therein. The receiving grooves 157 and 158 may be divided specifically into a first receiving portion 157 and a second receiving portion 158.

The first receiving portion 157 forms a space receiving one of the ribs as the rail 112. The second receiving portion 158 may include two receiving spaces arranged on both sides of the first receiving portion 157 and receiving one pair of the ribs. Here, the one pair of the ribs may be disposed opposite to each other on the both sides of the one of the ribs.

An opening 159 may be formed on an opposite side to the first receiving portion 157. Through the opening 159, the rail 112 may be received in the receiving grooves 157 and 158 by pressing the slider 156 against the main portion 111 in a direction perpendicular to the first central axis $C_1$.

Furthermore, the second receiving portion 158 of the slider 156 is a portion that is caught by the first stopper 113, whereas the first receiving portion 157 of the slider 156 is a portion that is caught by the second stopper 114. As a result, the second receiving portion 158 close to the opening 159 is easy to elastically deform, which is structurally advantageous for the slider 156 to pass over the first stopper 113.

Now, a blood collecting and ejecting mechanism will be described with further reference to FIG. 5.

Figure 5:
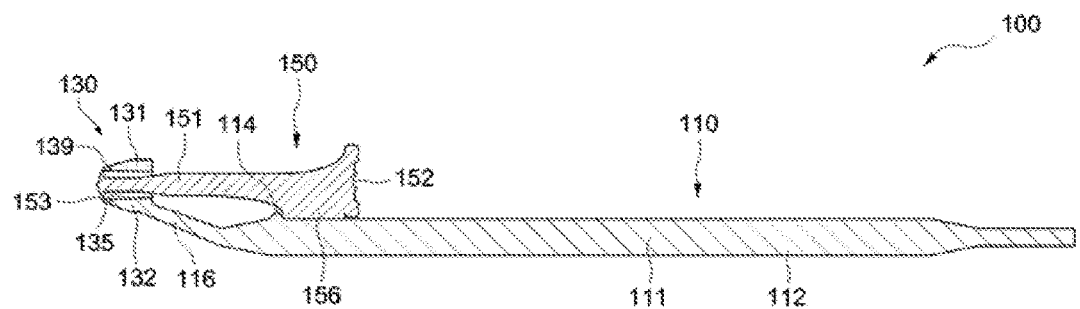
FIG. 5 is a cross-sectional view illustrating a state in which the plunger 150 is inserted into the handling block 130 in FIG. 2.

FIG. 5 is a cross-sectional view illustrating a state in which the plunger 150 is inserted into the handling block 130 in FIG. 2.

Referring to FIG. 5 (and FIGS. 1 to 4), the user may handle the blood using the handling block 130 in a state where the handle 110, in particular the main portion 111, is gripped in a user's hand.

To this end, the user first obtains blood drawn from a finger of a subject using a lancet or the like. Thereafter, when the handling block 130 is brought into contact with the blood drawn, the handling block 130 collects a preset amount of blood by the action of capillary force. Here, the plunger 150 is caught by the first stopper 113, so that the rod 151 or the squeezing plate 153 is not inserted into the collection port 135. Accordingly, the plunger 150 does not interfere with the capillary action by which the blood is collected in the collection port 135.

Next, the user places the handling block 130 on the absorption pad of the diagnostic device in a state where the handle 110 is gripped in the user's hand. Then, the blood collected in the handling block 130 may be ejected into the absorption pad by an absorbing force of the absorption pad.

In a case where there is a difficulty in ejecting the blood, the user may place a finger on the manipulation portion 152 of the plunger 150 and push the plunger 150 toward the handling block 130. Accordingly, the slider 156 of the plunger 150 sliders on the rail 112 along the direction of the first central axis $C_1$ and passes over the first stopper 113. As a result, the rod 151, in particular the squeezing plate 153, moves forward toward the handling block 130. Thereafter, the rod 151, in particular the squeezing plate 153, is inserted into the collection port 135, and the squeezing plate 153 is elastically deformed to exhaustively eject the blood in the collection port 135 into the absorption pad. The slider 156 moved in this way is finally caught and stopped by the second stopper 114 not to move down to the sub portion 116.

Thereafter, the user may check a simple diagnosis result of the blood with respect to a disease through the diagnostic device.

According to the unit for collecting and ejecting blood of the present invention configured as described above, when the handling block is brought into contact with blood in a state where the user is gripping the handle, a planned amount of blood is collected in the collection port, which is formed in the handling block to vertically pass therethrough, by a capillary force without being disrupted by an air layer. The collected blood can be forcedly ejected to the outside as the plunger, which is installed to be movable on the handle when manipulated, enters the collection port.

The above-described unit for collecting and ejecting blood is not limited to the configurations and the operation methods of the exemplary embodiments described above. Each of the above-described exemplary embodiments may also be combined either partially or entirely in a selective manner to make various modifications.

What is claimed is:

1. A unit for collecting and ejecting blood comprising:
 a handle extending along a first central axis;
 a handling block connected to the handle and disposed to have a second central axis that is offset from the first central axis;
 a plunger connected to the handle to be movable along a direction of the first central axis and moving toward the handling block when manipulated,
 wherein the handling block includes:
 a body having a connection portion connected to the handle and a contact portion located beneath the connection portion; and
 a collection port formed to pass through the body in a direction from the contact portion to the connection portion and configured to collect blood by a capillary force, and
 the plunger being movable along the handle along the direction of the first central axis when manipulated to enter the collection port and push the blood collected in the collection port out of the collection port, the plunger is aligned along the second central axis and is axially movable between first and second positions, wherein the plunger in the first position is located outside the handling block and the collection port for allowing the collection port to collect the blood by the capillary force, and the plunger in the second position extends through the handling block and the collection port,
 wherein the handle has an axial length that is greater than an axial length of the plunger to facilitate axial movement of the plunger and gripping of the handle by a user,
 the handle includes:
 a main portion extending along the first central axis; and
 a rail formed on the main portion and extending along the direction of the first central axis,
 the plunger includes a slider slidably coupled to the rail along the direction of the first central axis such that the plunger is connected to the handle and aligned on the second central axis in both the first and the second positions, and the handle includes stoppers formed on the main portion, the stoppers including:
- a first stopper that contacts the slider and stops the plunger at the first position outside the handling block and outside the collection port before the plunger enters the collection port; and
- a second stopper that contacts the slider and stops the plunger at the second position in which the plunger extends through the handling block and the collection port.

2. The unit for collecting and ejecting blood of claim 1, wherein the first stopper is formed to protrude at a height allowing the plunger to pass therethrough, and
the second stopper is formed to protrude at a height not allowing the plunger to pass therethrough.

3. A unit for collecting and ejecting blood comprising:
a handle having a length to be gripped in a hand of a user;
a handling block including a body connected to the handle and a collection port that extends axially through the body in a vertical direction and the collection port is formed to collect blood by a capillary force;
a plunger movably installed on the handle and configured to be inserted into the collection port to eject the blood collected in the collection port out of the collection port, the plunger is coaxially aligned with the collection port and is axially movable between first and second positions, wherein the plunger in the first position is located outside the handling block and the collection port for allowing the collection port to collect the blood by the capillary force, and the plunger in the second position extends through the handling block and the collection port; and
wherein the handle has an axial length that is greater than an axial length of the plunger to facilitate axial movement of the plunger along the handle and gripping of the handle by a user,
the handle includes:
- a main portion extending along a length direction and having an outer surface; and
- a rail formed on the outer surface of the main portion and extending along the length direction, the plunger includes a slider that is positionally fixed to the plunger, and the slider is slidably coupled to the rail such that the plunger and the slider move in unison along the length direction,
the plunger in the first position is secured to the handle such that the plunger is axially separated from the handling block,
the plunger in the second position is secured to the handle such that the plunger axially extends through the handling block and the collection port, and an axial length of the handling block is the same as an axial length of the collection port,
the handle includes stoppers formed on the main portion, the stoppers including:
- a first stopper that contacts the slider and stops the plunger at the first position outside the handling block and outside the collection port before the plunger enters the collection port; and
- a second stopper that contacts the slider and stops the plunger at the second position in which the plunger extends through the handling block and the collection port.

4. The unit for collecting and ejecting blood of claim 3, wherein the rail includes a rib protruding from the outer surface of the main portion in a radial direction, and
the slider includes a receiving groove which receives the rib and extends along the length direction such that the slider and the plunger are only movable relative to the handle along the length direction.

5. The unit for collecting and ejecting blood of claim 3, wherein the plunger further includes a rod connected to the slider and disposed to be inserted into the collection port.

6. The unit for collecting and ejecting blood of claim 5, wherein the plunger further includes a squeezing plate installed at a front end of the rod is configured to be elastically deformed, the squeezing plate having a larger cross-sectional area than the rod.

* * * * *